United States Patent [19]
Swensen

[11] Patent Number: 6,150,514
[45] Date of Patent: Nov. 21, 2000

[54] 14 KILOBASE DELETION IN THE PROMOTER REGION OF BRCA1 IN A BREAST CANCER FAMILY

[75] Inventor: Jeff Swensen, Salt Lake City, Utah

[73] Assignee: University of Utah Research Foundation, Salt Lake City, Utah

[21] Appl. No.: 09/056,762

[22] Filed: Apr. 8, 1998

Related U.S. Application Data

[60] Provisional application No. 60/043,116, Apr. 9, 1997.

[51] Int. Cl.[7] ................................................. C07H 21/04
[52] U.S. Cl. .............................. 536/23.5; 536/23.1
[58] Field of Search .................................. 536/23.1, 23.5; 435/6

[56] References Cited

PUBLICATIONS

Puget, N. et al., "A 1–kb Alu–mediated Germ–line Deletion Removing BRCA1 Exon 17", Cancer Research (1997) 57:828–831, Mar. 1997.

Ariga, T. et al., "Recombinations between Alu Repeat Sequences That Result in Partial Deletions within the C1 Inhibitor Gene", Genomics (1990) 8:607–613.

Brown, M.A., et al., "The 5' end of the BRCA1 gene lies within a duplicated region of human chromosome 17q21", Oncogene (1996) 12:2507–2513.

Huang, L–S, et al., "Hypobetalipoproteinemia Due to an Apolipoprotein B Gene Exon 21 Deletion Derived by Alu––Alu Recombination", The Journal of Biological Chemistry (Jul. 5, 1989) 264:11394–11400.

Miki, Y., et al., "A Strong Candidate for the Breast and Ovarian Cancer Susceptibiligy Gene BRCA1", Science (Oct. 7, 1994) 266:66–71.

Neote, K., et al., "Structure and Distribution of an Alu–type Deletion Mutation in Sandhoff Disease", J. Clin. Invest. (Nov. 1990) 86:1524–1531.

Serova, O., et al., "A High Incidence of BRCA1 Mutations in 20 Breast–Ovarian Cancer Families", Am. J. Hum. Genet. (1996) 58:42–51.

Smith, T.M., et al., "CompleteGenomic Sequence and Analysis of 117 kb of Human DNA Containing the Gene BRCA1", Genome Research (1996) 6:1029–1049.

Szabo, C.I. and King, M., "Inherited breast and ovarian cancer", Human Molecular Genetics (1995) 4:1811–1817.

Xu, C–F, et al., "Distinct transcription start sites generate two forms of BRCA1 mRNA", Human Molecular Genetics (1995) 4(12):2259–2264.

GenBank Accession No. L78833. World Wide Web URL: http://www2.ncbi.nlm.nih.gov/.

PubMed Accession No. U37574. World Wide Web URL: http://www.ncbi.nlm.nih.gov/.

*Primary Examiner*—Stephanie W. Zitomer
*Assistant Examiner*—Bj Forman
*Attorney, Agent, or Firm*—Rothwell, Figg, Ernst & Manbeck P.C.

[57] ABSTRACT

A 14 kb deletion in the promoter region of a BRCA1 gene has been found in a kindred which had earlier been linked to BRCA1. This deletion is apparently the result of unequal crossing over between two Alu repeats, one of which is 5' upstream of the start of the coding region and the second which is within intron 2. The deletion results in exons 1a, 1b and 2 being deleted from the gene with the result that the gene cannot be transcribed.

5 Claims, 5 Drawing Sheets

FIG. 3A Bam HI
FIG. 3B Hind III
FIG. 3C Eco RV

SEQUENCE LISTING

<160> NUMBER OF SEQ ID NOS: 11

<210> SEQ ID NO 1
<211> LENGTH: 20
<212> TYPE: DNA
<213> ORGANISM: Homo sapiens

<400> SEQUENCE: 1
aactccagcg acagagctaa                                                        20

<210> SEQ ID NO 2
<211> LENGTH: 22
<212> TYPE: DNA
<213> ORGANISM: Homo sapiens

<400> SEQUENCE: 2
tgtatgtaca gagccagttt ca                                                     22

<210> SEQ ID NO 3
<211> LENGTH: 22
<212> TYPE: DNA
<213> ORGANISM: Homo sapiens

<400> SEQUENCE: 3
ccactgagga cctaaagcat aa                                                     22

<210> SEQ ID NO 4
<211> LENGTH: 24
<212> TYPE: DNA
<213> ORGANISM: Homo sapiens

<400> SEQUENCE: 4
gatattgtag ggaaagacta tcag                                                   24

<210> SEQ ID NO 5
<211> LENGTH: 25
<212> TYPE: DNA
<213> ORGANISM: Homo sapiens

<400> SEQUENCE: 5
gggataaggg aattaacatt tatgg                                                  25

<210> SEQ ID NO 6
<211> LENGTH: 23
<212> TYPE: DNA
<213> ORGANISM: Homo sapiens

<400> SEQUENCE: 6
ttagctttct tctgaatgtg aac                                                    23

<210> SEQ ID NO 7
<211> LENGTH: 75
<212> TYPE: DNA
<213> ORGANISM: Homo sapiens

<400> SEQUENCE: 7
ggcacaagaa tcacttcaat ccgagaggca gaggttgcag tgagccaaga ccacaccact            60
gcactccagc ctgag                                                             75

<210> SEQ ID NO 8
<211> LENGTH: 73

```
<212> TYPE: DNA
<213> ORGANISM: Homo sapiens

<400> SEQUENCE: 8
agcaggagaa ctgcttgaac ccggagcaga ggttgcagtg agccaagatc acgccactgc      60
actccagcct ggt                                                        73

<210> SEQ ID NO 9
<211> LENGTH: 37
<212> TYPE: DNA
<213> ORGANISM: Homo sapiens

<400> SEQUENCE: 9
acccggagca gaggttgcag tgagccaaga ccacacc                              37

<210> SEQ ID NO 10
<211> LENGTH: 148
<212> TYPE: DNA
<213> ORGANISM: Homo sapiens
<220> FEATURE:
<221> NAME/KEY: unsure
<222> LOCATION: (105)
<223> OTHER INFORMATION: The identity of this base is uncertain.

<400> SEQUENCE: 10
tttttgcagc tgctgtgtgc tggagctgtg ggaacccctc ggtaatctct tgtctgcttt      60
ttaggaactc ctatctccag atcttctttt acttcccaag ccacnccact tctttgaaag     120
gtctgcaggc ttgtctacct cttctcag                                       148

<210> SEQ ID NO 11
<211> LENGTH: 201
<212> TYPE: DNA
<213> ORGANISM: Homo sapiens

<400> SEQUENCE: 11
gctctagaac tagtggatcc cacttctcct gtccctgcc ctcaccactg aggacctaaa       60
gcataataaa agggacaat ctctgcccta aataatccct tttggcagtt actttctgtt     120
ttcaaacttc aaatctgtcc tctgggacta acctaggaga tgagggataa gggaattaac    180
atttatggaa aatggaggaa c                                              201
```

14 KILOBASE DELETION IN THE PROMOTER REGION OF BRCA1 IN A BREAST CANCER FAMILY

This appln claims the benefit of U.S. Provisional No. 60/043,116 filed Apr. 9, 1997.

This invention was made with Government support under Grant No. 55914 awarded by the National Institutes of Health, Bethesda, Md. The United States Government has certain rights in the invention.

BACKGROUND OF THE INVENTION

The present invention relates to alterations in the BRCA1 gene and methods for detecting such alterations.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Breast cancer is the most common cancer in women and its impact on mortality and morbidity is significant and well documented (American Cancer Society, 1996). The etiology of breast cancer is related to hormonal, genetic, and environmental factors. From epidemiologic studies the increase in breast cancer risk associated with reproductive and other hormonal factors, diet, alcohol consumption and other environmental and host factors accounts for less than 50% of cases (Kelsey, 1993). Breast cancer affects one in eight women, and is their second leading cause of death from cancer (Boring et al., 1994), whereas ovarian cancer, although less frequent, is the leading cause of death from gynecologic malignancies in North America. It is estimated that 5–10% of breast cancer cases may be due to inherited autosomal dominant susceptibility genes (Claus et al., 1991; Hoskins et al., 1995). Ovarian cancer is also known to have a familial component (Schildkraut et al., 1988; Cannon-Albright, 1994).

Breast cancer occurs in hereditary and sporadic forms. Hereditary breast cancers are genetically heterologous. Susceptibility is variously attributable to germline mutations in the BRCA1 gene (Miki et al., 1994), BRCA2 gene (Wooster et al., 1995, Tavtigian et al., 1996), TP53 gene (Malkin et al., 1990) or ataxia telangiectasia gene (Savitsky et al., 1995), each of which is considered to be a tumor suppressor. Female BRCA1 mutation carriers are estimated to have an 87% lifetime risk of developing breast cancer and a 44% risk of ovarian cancer in breast/ovarian families (Easton et al., 1993; Steichen-Gersdorf et al., 1994; Narod et al., 1995; Easton et al., 1995; Ford et al., 1995; Ford et al., 1994). Moreover, BRCA1 carriers have a four-fold increased risk of colon cancer, whereas male carriers face a three-fold increased risk of prostate cancer (Ford et al., 1994). Mutations in the BRCA1 gene account for approximately 45% of familial breast cancer and 90% of inherited breast/ovarian cancer (Miki et al., 1994; Szabo and King, 1995). In addition, BRCA2 carriers have an increased risk of pancreatic cancer. Mutations in the BRCA2 gene account for a comparable percentage of inherited breast cancer cases (Wooster et al., 1995; Tavtigian et al., 1996). Over 85 distinct BRCA1 mutations and a growing list of BRCA2 mutations have been identified, with the majority resulting in protein truncation (The Breast Cancer Information Core). In addition, a wide array of polymorphic variants have been seen for both BRCA1 and BRCA2.

The BRCA1 gene contains 5592 bp of coding sequence encompassed within 23 exons spread over more than 70 kb of genomic DNA and encodes a protein of 1863 amino acids. The BRCA2 gene contains 10,443 bp of coding sequence encompassed within 27 exons spread over roughly 70 kb of genomic DNA and encodes a protein of 3418 amino acids.

Identification of the high risk of breast and ovarian cancer due to genetic defects in BRCA1 has led to an enormous effort to identify the spectrum of mutational lesions that occur in this gene. Thus, it is desired to identify additional alterations, including mutations and polymorphisms, which are present in the BRCA1 gene. Such alterations are useful in analysis of an individual's risk to develop breast and ovarian cancer as a result of such alterations.

SUMMARY OF THE INVENTION

The present invention relates to deletions in the promoter region of a BRCA1 gene in a breast cancer family and methods for detecting such deletions. A 14 kb deletion, which removes promoter region of BRCA1 and includes exons 1a, 1b and 2, has been found in a kindred which had been earlier linked to the BRCA1 gene. The deletion is the result of unequal crossing over between Alu repeats, with one repeat in the 5' upstream region and the other repeat in intron 2. Any method which is capable of detecting the deletions described herein can be used. Such methods include, but are not limited to, DNA sequencing, Southern blotting, and PCR amplification.

DETAILED DESCRIPTION OF THE INVENTION

Figure 1:
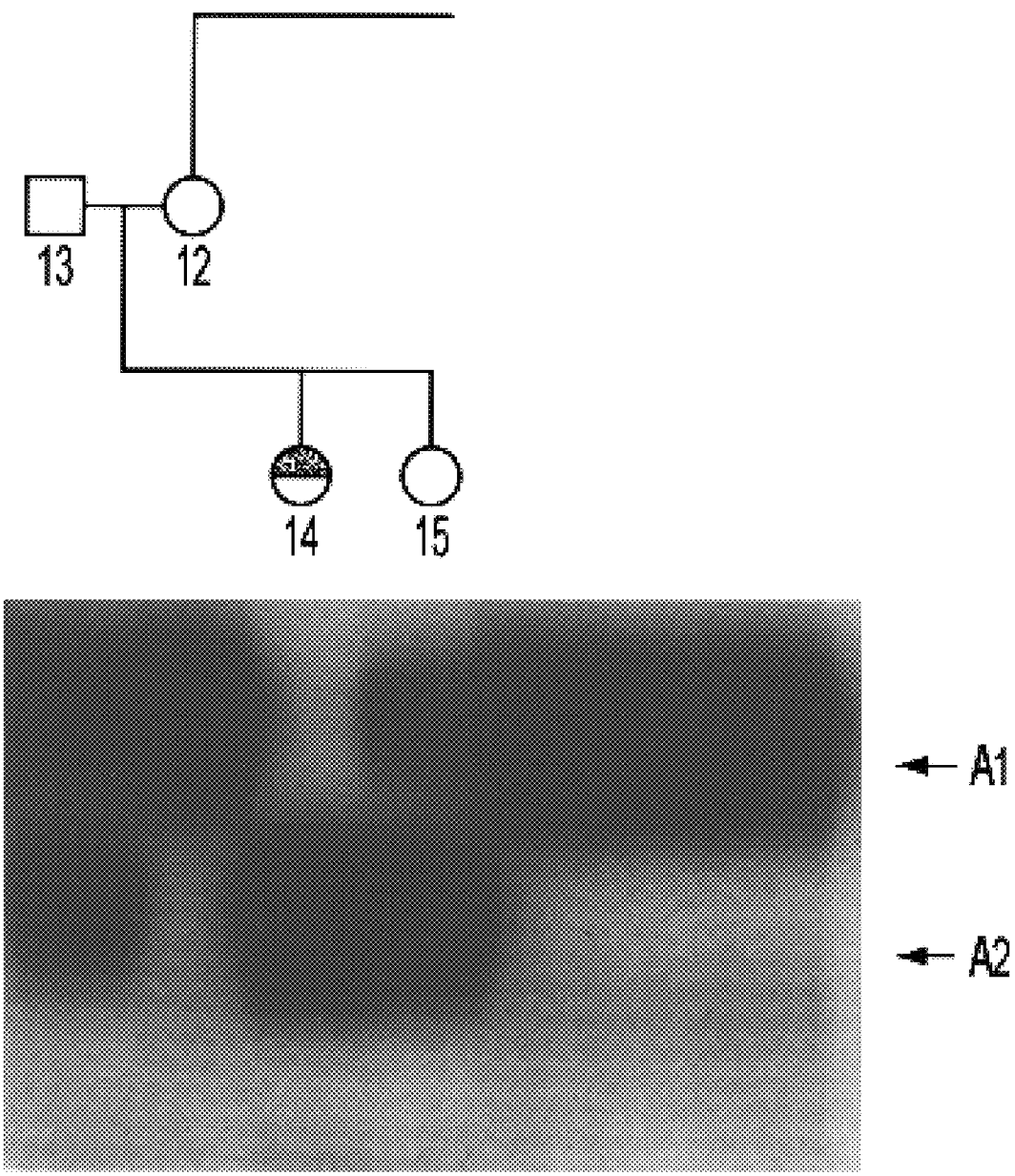
FIG. 1 shows amplification of the intron 2 polymorphism in the branch of K2035 which demonstrates the hemizygosity of haplotype carriers. The affected daughter (#14) received allele 2 (A2) from her father (#13), but did not receive allele 1 (A1) from her apparently homozygous, haplotype-carrying mother (#12). The heterozygous sibling (#15) does not carry the haplotype.

The present invention relates to deletions in the BRCA1 gene and methods for detecting such deletions. Any method which is capable of detecting the deletions described herein can be used. Such methods include, but are not limited to, DNA sequencing, Southern blotting, and PCR amplification.

BRCA1 is a breast and ovarian cancer susceptibility gene. An inferred germline regulatory mutation was previously reported in the BRCA1-linked kindred K2035, based on the absence of transcripts from the BRCA1 allele associated with the cancer susceptibility haplotype. In this study, the promoter region of BRCA1 was examined in individuals from K2035 for evidence of a mutation which could halt transcription. Evaluation of a polymorphism located in BRCA1 intron 2 gave results consistent with the presence of a large deletion in haplotype carriers. Southern blot analysis identified unique restriction fragments in K2035 haplotype carriers which occurred as a result of a 14 kb deletion that removed both of BRCA1's transcription start sites (exons 1a and 1b) as well as exon 2. Sequencing indicated that unequal crossover between Alu repeats was the cause of the deletion. Similar deletions may be responsible for other reported inferred regulatory mutations as well as unidentified mutations in families linked to BRCA1.

Germline mutations in BRCA1 cause a hereditary predisposition to breast and ovarian carcinomas. Mutations are distributed throughout the gene and most frequently lead to truncation of the protein. It has been estimated that mutations which affect expression, splicing or stability of the transcript may account for 15–20% of the total (Szabo and King, 1995). In a previous study, mutation carrier status of a BRCA1-linked kindred, K2035, had been assigned based upon a shared haplotype segregating with breast or ovarian cancers (haplotype carriers). It was determined that genomic DNA of a haplotype carrier from K2035 was heterozygous for a series of polymorphisms in the distal 3.5 kb of BRCA1, while cDNA from the same individual appeared homozygous at the loci (Miki et al., 1994). The presence of a regulatory mutation which halted transcription from the shared allele was inferred based on these results. A similar loss of transcription from BRCA1 has been reported in three additional families (Gayther et al., 1995; Serova et al., 1996), suggesting such mutations occur at some frequency.

Alu repeats are frequently associated with the formation of large deletions (Ariga et al., 1990; Huang et al., 1989; Neote et al., 1990) and the BRCA1 genomic sequence is rich in such elements. The BRCA1 gene contains numerous Alu repeats. This can be seen from examining the "Features" section of Genbank Accession Number L78833 which includes the complete genomic sequence for BRCA1 (Smith et al., 1996). One can use this known sequence to design probes or primers to search for deletions within BRCA1 which could have occurred as a result of unequal crossing-over between Alu repeats. For example, one could design primers outside each of two Alu repeats and use these in a PCR to determine the size of any amplified fragment and compare this with the size obtained from a wild-type sample. Often one may have primers which are so far apart in the wild-type BRCA1 gene that no amplification will occur with a wild-type sample but amplification will occur with a sample containing a deletion which results in the two primers being that much closer to each other and therefore being able to produce an amplified product.

In the present study, the promoter region of BRCA1 was studied in K2035 haplotype carriers for evidence of a mutation which could halt transcription from the gene. A 14 kb deletion which removed exons 1a, 1b and 2 was identified. Sequence analysis revealed that the deletion occurred as a result of unequal crossover between Alu repeats. This result suggests a possible genomic basis for other inferred BRCA1 regulatory mutations.

A mutation affecting the promoter region was considered a likely reason for the absence of transcription from the BRCA1 allele associated with the K2035 susceptibility haplotype. The structure of the promoter region of the gene had been reported (GenBank number: U37574) (Xu et al., 1995). Transcription was found to start from one of two alternatively spliced first exons (exon 1a or 1b). Both variants were represented in the tissue types examined in the study, thus, a mutation which halted transcription from BRCA1 would have to affect two regions. Alu repeats are frequently associated with the formation of large deletions (Ariga et al., 1990; Huang et al., 1989; Neote et al., 1990) and the BRCA1 genomic sequence is rich in repetitive areas. A large deletion could remove both promoter regions and thereby stop transcription.

To rule out a deletion, genomic sequence at the 5' end of BRCA1 was surveyed for polymorphisms which could potentially demonstrate the heterozygosity of haplotype carriers. PCR primers were designed around a poly(A) tract of an Alu repeat in intron 2. The PCR product obtained using these primers was ~130 bp, the exact length depending upon the polymorphism which was found. This sequence corresponds to bases 5331–5458 of GenBank Accession Number L78833 (Smith et al., 1996). The product was amplified from the DNA of several K2035 carriers and electrophoresed. All individuals appeared homozygous, however, one had an allele (allele 2) which was a different size than the allele in the others (allele 1). Thus, the haplotype was seemingly not conserved.

DNA preparations from the parents and a sibling of the individual with allele 2 were amplified with the primer set (FIG. 1). The non-haplotype carrying father and sibling were heterozygous (alleles 1, 2) while the haplotype carrying mother appeared homozygous (allele 1). No amplification was seen from the mother's chromosome in the affected daughter. Although this could have resulted from a localized alteration in the sequence, it was consistent with the locus being hemizygous in haplotype carriers due to a deletion.

A 60 kb P1 clone (1141) was known to extend from exon 11 through the promoter region of BRCA1 (Neuhausen et al., 1994). This clone is commercially available from Genome Systems, Inc. (St. Louis, Mo.) as address 1363C4 of the P1 library. Digestion of P1 1141 with EcoRI, HindIII, BamHI and EcoRV restriction endonucleases yielded fragments used to construct a restriction map (FIG. 2), that was later supplemented with the recently published BRCA1 genomic sequence (GenBank number: L78833) (Smith et al., 1996). Since it had previously been demonstrated that haplotype carriers were heterozygous in exon 11 (Miki et al., 1994), the search for a lower deletion breakpoint was limited to the region between exon 2 and exon 11.

Southern blot analysis was performed using DNA preparations from one K2035 haplotype carrier and one noncarrier which were digested individually with HindIII, EcoRI, BamHI, EcoRV, BglII and PvuII. PCR products obtained from the promoter-distal ends of EcoRI restriction fragments were used as hybridization probes. Hybridization with probe "A" from intron 2 (FIG. 2) revealed unique bands in the haplotype carrier on BamHI, EcoRV, BglII and PvuII blots. This result was consistent with the presence of a deletion breakpoint.

Figure 2:
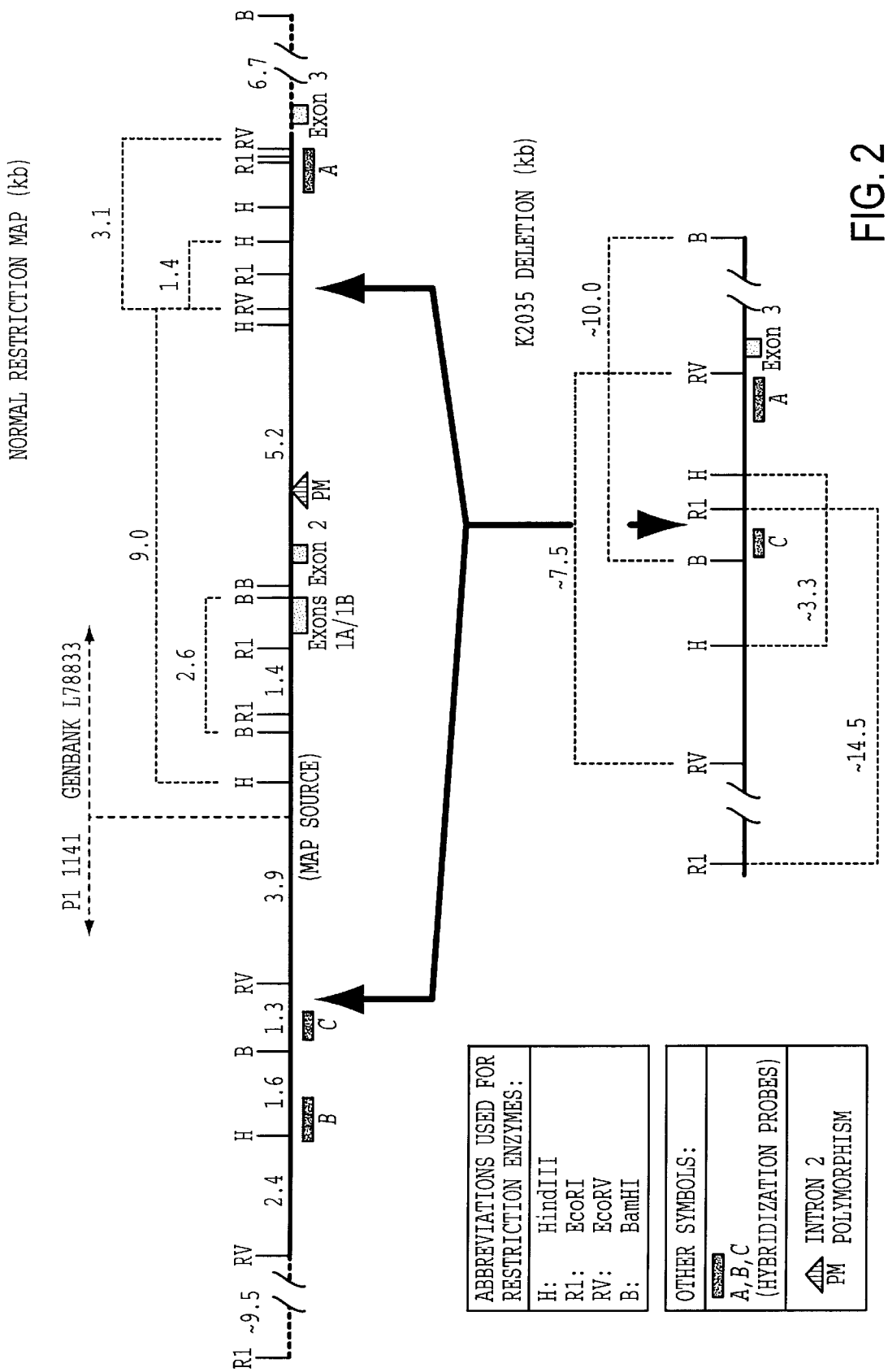
FIG. 2 shows a restriction map of the genomic region affected by the 14 kb deletion. The upper map shows the normal 5' end of BRCA1. Arrows mark the locations of the deletion breakpoints. The lower map shows only the restriction sites involved in producing the unique fragments in deletion carriers. The arrow marks the joined area. Distances are in kilobases.
Figure 3:
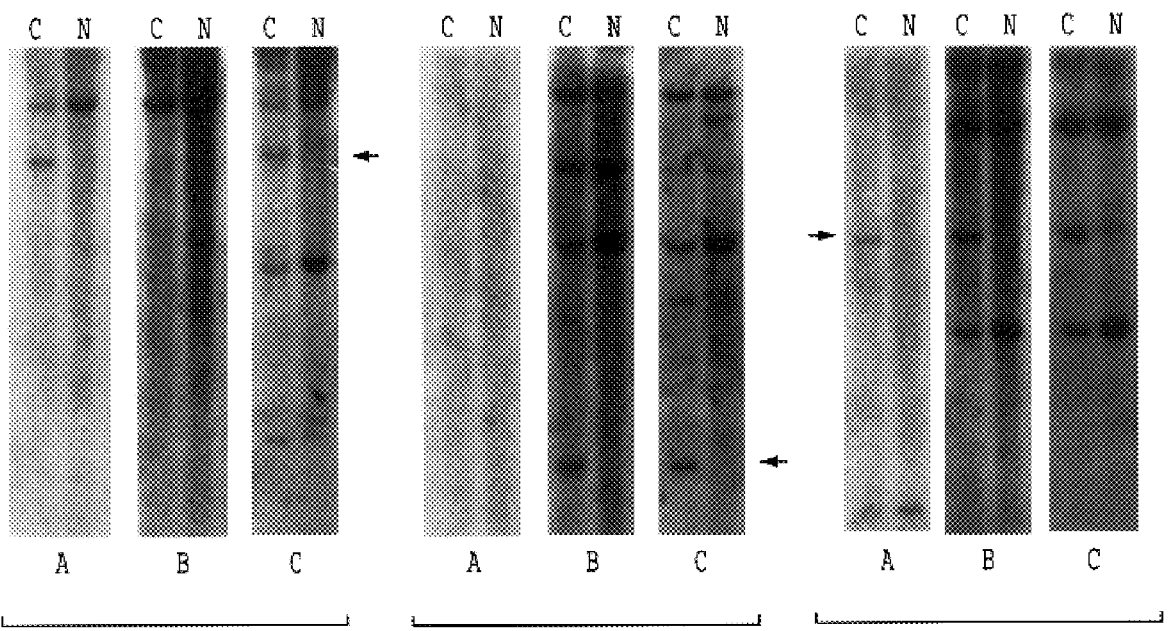
FIGS. 3A–3C show Southern blots made from the DNA of K2035 haplotype carriers (C) and noncarriers (N). The enzyme used to produce each blot is indicated. The blots have been sequentially hybridized with probes "A, B and C". Unique bands which result from the deletion are labeled with arrows.

Probe "B" (FIG. 2) was used to locate the upper deletion breakpoint which was presumed to lie across the BRCA1 promoter. This probe hybridized to a unique EcoRV band in the haplotype carrier which corresponded to the one identified with probe "A". Altered HindIII (FIG. 3B) and EcoRI bands were also identified. Probe "C" (FIG. 2), which was located closer to the breakpoint, revealed unique bands of the expected sizes with all six enzymes in the haplotype carrier. FIGS. 3A–3C demonstrate this for the enzymes BamHI, HindIII and EcoRV. These results were consistent with the presence of a 14 kb deletion which spanned the BRCA1 promoter region (FIG. 2).

Probes "B" and "C" hybridized to multiple sets of normal bands in most of the blots. This presumably occurred as a result of the ~30 kb duplication which was identified in this region (Brown et al., 1996). These extra bands produced a more complex hybridization pattern, but did not interfere with the identification of unique fragments.

Figure 4:
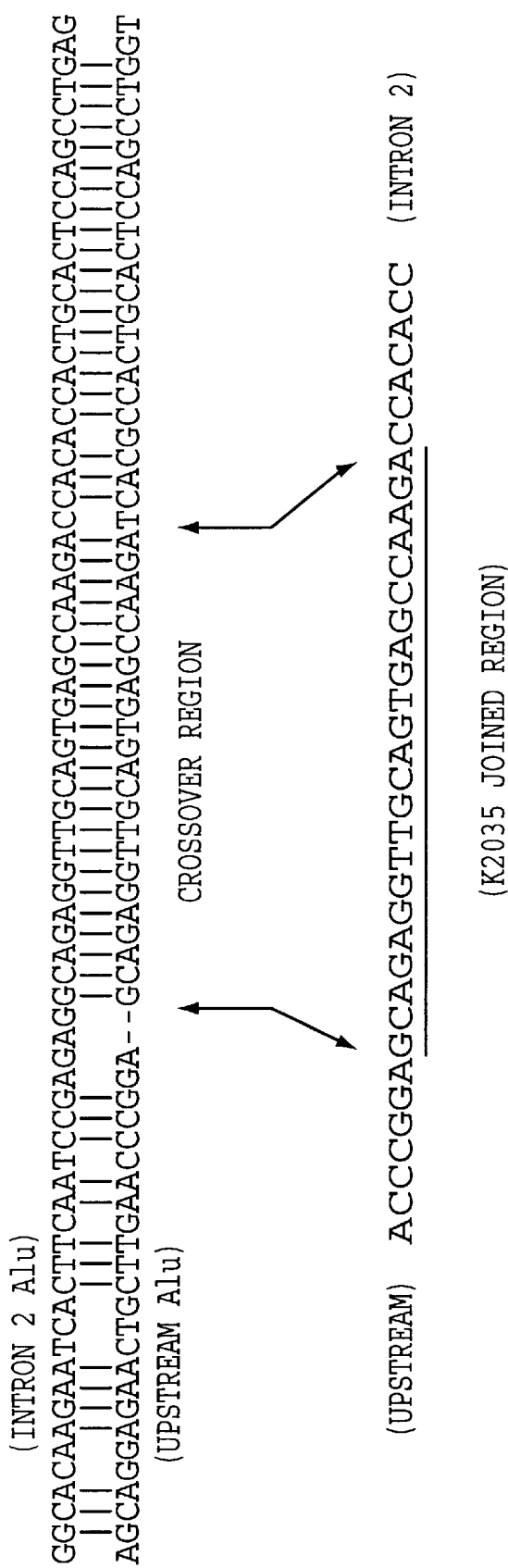
FIG. 4 shows the alignment of the Alu repeats involved in the unequal crossover in K2035 haplotype carriers. Recombination occurred in the region between the arrows. The intron 2 Alu corresponds to bases 9857–9931 of GenBank Accession Number L78833 (Smith et al., 1996). The intron 2 Alu sequence is shown as SEQ ID NO:7 in the Sequence Listing. The upstream Alu sequence is shown as SEQ ID NO:8 in the Sequence Listing. The sequence shown as the joined region sequence is presented as SEQ ID NO:9 in the Sequence Listing.

Oligonucleotides were designed to amplify a PCR product across the deletion. PCR primers, which were normally ~15 kb apart, specifically amplified a 1.3 kb product in the haplotype carriers which could be reamplified with nested primers into a 650 bp product. Sequencing revealed that the PCR product contained the expected sequence on each of its ends. Within the product, the right arm of an Alu repeat in intron 2 was found to be joined to an Alu fragment from the upstream region in a way which preserved the consensus sequence of an Alu element (FIG. 4). By upstream is meant a region which is farther to the left on a map of the gene when the map shows exons in the order 1a, 1b, 2, 3, etc. from left to right. Therefore, exon 1a is upstream of exon 2, exon 2 is upstream of exon 3, etc. By downstream is meant a region which is farther to the right on a map of the gene when the map shows exons in the order 1a, 1b, 2, 3, etc. from left to right. Therefore, exon 3 is downstream from exon 2, exon 2 is downstream from exon 1b, etc. When considering a fragment of a gene, an upstream portion is a part of the fragment which is located toward the 5' end and a downstream portion is a part of the fragment which is located toward the 3' end wherein the 5' end is to the left and the 3' end is to the right on a map as defined above. The promoter portion of the gene contains sequence including 5'-untranslated sequence which is upstream from exon 1a. The joined Alu fragment was consistent with the deletion having occurred as a result of unequal crossover between the Alu sequences in a region of 23 bp of perfect sequence similarity.

Figure 5:
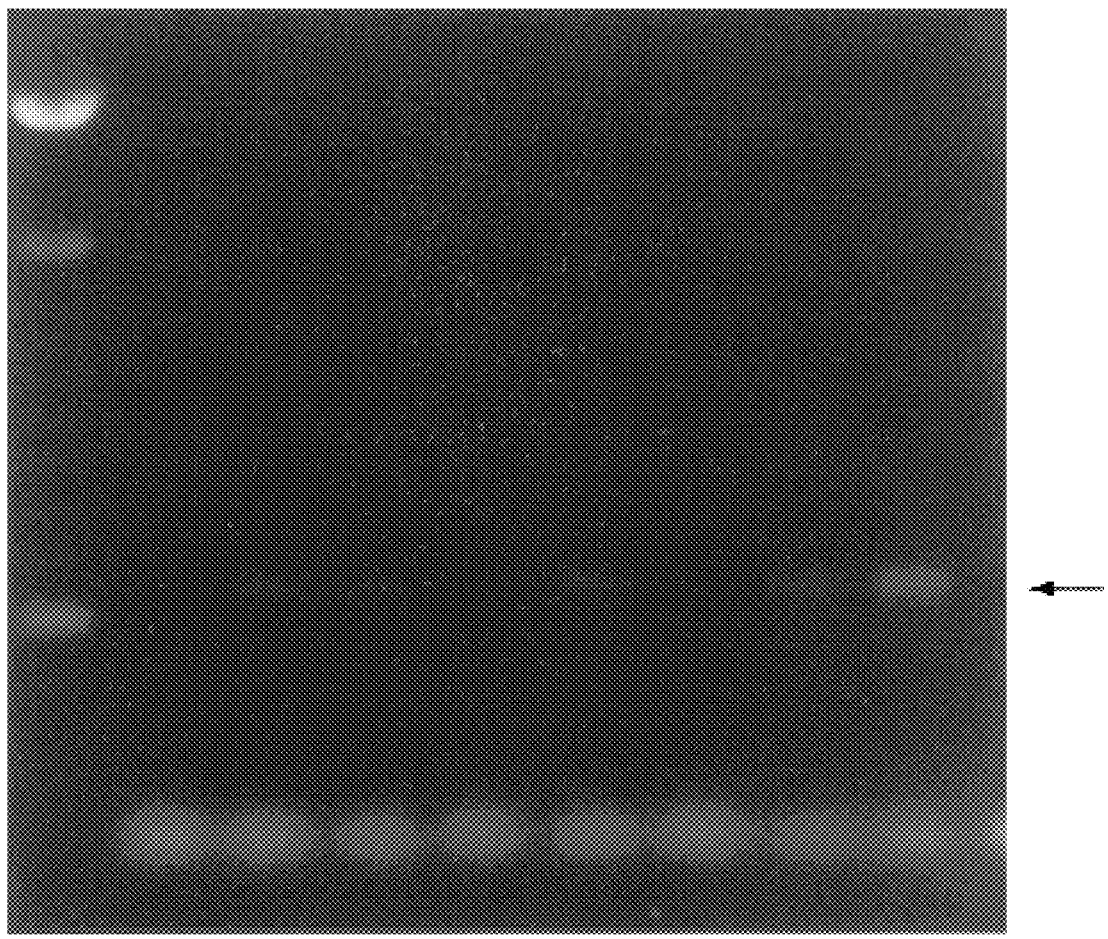
FIG. 5 shows the agarose gel electrophoresis demonstrating the specific amplification of the 650 bp PCR product (arrow) which spans the junction of the 14 kb deletion. All PCR reactions were successful as seen by the ~300 bp control band. The 650 bp band amplified only in K2035 haplotype carriers.

The PCR product spanning the deletion was amplified in 55 individuals and their spouses from K2035 (see example in FIG. 5). An additional 50 random individuals were examined to confirm the specificity of the PCR product. Amplification occurred only in the 23 haplotype carriers. These results were consistent with previous haplotype analysis for six markers across a 625 kb region spanning the BRCA1 gene. Eight of the ten breast cancer cases in the family were tested and all eight carried the mutation. The ninth case was deceased and inferred to be a mutation carrier as several of her children were positive and her spouse was negative. It was not possible to determine the mutation status of the tenth case.

Only breast cancers and one ovarian cancer are seen in K2035. There are no prostate or colon cancers, which are often present in BRCA1 families, although there are three obligate male mutation carriers in their 60's. The breast cancer cases in this family descend from two sisters who were both unaffected until their deaths in their 80's. There is an additional obligate female carrier in her 60's who has not had any cancer. Lifetime cumulative penetrance was estimated at 85% and by age 50 was 75%. This is higher than the 59% cumulative overall reported for BRCA1 at age 50 (Ford et al., 1994), although it is not significant due to the large confidence intervals associated with the small sample size.

The results obtained indicate the presence of a 14 kb deletion which prevents transcription of the shared BRCA1 allele in K2035 haplotype carriers by removing both transcription start sites. Exon 2 is also eliminated. Similar mutations affecting the BRCA1 promoter region may be responsible for inferred regulatory mutations in other reported families (Gayther et al., 1995; Serova et al., 1996). There are additional kindreds with significant evidence for linkage to BRCA1 in which mutations have not been identified. No cDNA analysis had been performed, so loss of transcript mutations may be present in a percentage of these as well.

In order to detect the presence of alterations in the BRCA1 gene, a biological sample such as blood is prepared and analyzed for the presence or absence of a given alteration of BRCA1. In order to detect the presence of neoplasia, the progression toward malignancy of a precursor lesion, or as a prognostic indicator, a biological sample of the lesion is prepared and analyzed for the presence or absence of a deletion of BRCA1 or a portion thereof. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis.

Initially, the screening method involves amplification of the relevant BRCA1 sequences. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity. Further details of these methods are briefly presented below and further descriptions can be found in PCT published application WO 96/05306, incorporated herein by reference.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences (for example, in screening for cancer susceptibility), the biological sample to be analyzed, such as blood or serum, may be treated, if desired, to extract the nucleic acids. The sample nucleic acid may be prepared in various ways to facilitate detection of the target sequence; e.g. denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of human chromosome 17. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g., nick translation, random priming or kinasing), biotin, fluorescent groups, chemiluminescent groups (e.g., dioxetanes, particularly triggered dioxetanes), enzymes, antibodies and the like. Variations of this basic scheme are known in the art, and include those variations that facilitate separation of the hybrids to be detected from extraneous materials and/or that amplify the signal from the labeled moiety. A number of these variations are well known.

As noted above, non-PCR based screening assays are also contemplated in this invention. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For example, the preparation of oligodeoxynucleotide-alkaline phosphatase conjugates and their use as hybridization probes are well known.

Two-step label amplification methodologies are known in the art. These assays work on the principle that a small ligand (such as digoxigenin, biotin, or the like) is attached to a nucleic acid probe capable of specifically binding BRCA1. An allele specific probe is also contemplated within the scope of this example.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. In a second example, the small ligand is recognized by a second ligand-enzyme conjugate that is capable of specifically complexing to the first ligand. A well known embodiment of this example is the biotin-avidin type of interactions. Methods for labeling nucleic acid probes and their use in biotin-avidin based assays are well known.

The present invention is described by reference to the following Examples, which are offered by way of illustration and are not intended to limit the invention in any manner. Standard techniques well known in the art or the techniques specifically described below were utilized.

EXAMPLE

The methods used to study family K2035 which revealed the 14 kb deletion which included exons 1a, 1b and 2 are detailed as follow. These methods were used to obtain the results which were disclosed above.

Family

K2035 is a family which self-referred. All participants signed informed consent documents, and this research project was approved by the University of Utah School of Medicine Institutional Review Board. Individuals completed a questionnaire and gave a sample of blood. The family was extended to all possible mutation carriers and their relatives. It is an extended family of 55 individuals, including spouses, with 7 cases of unilateral breast cancer (age of onset 27 to 53 years), 2 cases of bilateral breast cancer (age of onset 33/34 and 46/55 years) and one case of bilateral breast and ovarian cancer (diagnosed at age 45 and 62 with breast cancer and age 59 years with ovarian cancer). It had been linked previously to BRCA1 with a Lod score of 2.25 at D17S1327 (Miki et al., 1994). Haplotype carrier status had been assigned based on a shared, six-marker haplotype segregating with the disease.

DNA Extraction

Nuclear pellets were prepared from 16 ml of ACD blood, then extracted with phenol and chloroform. DNA was precipitated with ethanol, and resuspended in Tris-EDTA.

Restriction Mapping

DNA from P1 1141 was digested with HindIII and EcoRI, and Southern blots were prepared. BRCA1 exons 2–11 were radiolabeled by PCR, then hybridized singly and in combination to the blot. Some EcoRI fragments were also used as probes. A restriction map was created based on the locations of the exons, hybridization of EcoRI fragments, double digests, and bands shared with other clones in the region. Recently published BRCA1 genomic sequence (GenBank number: L78833) (Smith et al., 1996) was used to confirm and complete the map. Additional mapping was later performed with EcoRV and BamHI.

Hybridization Probes and Sequencing

Restriction fragments were cut from agarose gels and purified with a Geneclean® kit (BIO 101). A vector [pBluescript® (Stratagene)], digested to have a compatible end and treated with calf intestinal phosphatase, was then ligated onto one or both ends of the fragments so the random priming technique (RPT) could be used as previously described (Swensen, 1996) to create PCR products using one specific primer in combination with an array of single, randomly selected oligonucleotides. After incubation the ligations were diluted 1:100 for use as PCR templates. T3 and T7 oligonucleotides were used as specific primers for the RPT. Products were sequenced with a Cyclist™ kit (Stratagene) to determine if repetitive sequence was present which would interfere with their use as hybridization probes. A probe's location on the restriction map was confirmed by its pattern of hybridization to the blots.

Probe "A" was obtained from the region around the promoter-distal end of a 2.3 kb EcoRI fragment located upstream of exon 3. It corresponds to bases 12425–12790 of GenBank Accession Number L8833 (Smith et al., 1996). Probe "B" was created on the promoter-distal end of a 6.8 kb HindIII fragment located upstream of the first exon. Probe "B" has been partially sequenced and its partial sequence is shown as SEQ ID NO:10 in the Sequence Listing. A probe based upon SEQ ID NO:10 can be used for the same purposes as the complete probe "B". Since probe "B" detected an altered band on the EcoRV blot, but not the BamHI blot, the breakpoint was localized to a 1.3 kb BamHI/EcoRV fragment. Probe "C" was obtained from this fragment. Probe "C" has been partially sequenced and its partial sequence is shown as SEQ ID NO:11 in the Sequence Listing. SEQ ID NO:11 includes SEQ ID NO:3 and SEQ ID NO:5 within it, SEQ ID NO:3 corresponding to bases 45–66 of SEQ ID NO:11 and SEQ ID NO:5 corresponding to bases 164–188 of SEQ ID NO:11. A probe based upon SEQ ID NO:11 can be used for the same purposes as the complete probe "C". The probes ranged in size from 350 bp to 600 bp in length, including the vector sequence each contained, although as noted shorter probes based upon SEQ ID NO:10 and SEQ ID NO:11 are equally as good. The probes were chosen such that they did not contain Alu repeat sequence within them.

Southern Blot Analysis

DNA preparations from one haplotype carrier and one noncarrier (5 µg for each) were digested individually with EcoRI, HindIII, EcoRV, PvuII and BglII. The digests were electrophoresed on a 0.8% agarose gel and transferred to Hybond™-N+ nylon membrane (Amersham). Blots were crosslinked by exposure to UV light and were prehybridized for two hours at 65° C. in a solution consisting of 10% PEG 8000, 7% SDS, 5×SSPE and 200 µg/mL sheared salmon sperm DNA which had been boiled prior to addition.

Probes for hybridization consisted of RPT PCR products which were reamplified in a 30 µL volume for 45 cycles. Reaction mixes contained 200 µM dGTP, dTTP and dATP; 5 µM dCTP; 15 µCi [$\alpha^{32}$P]dCTP; 0.5 µM each primer, 1 unit of AmpliTaq® DNA Polymerase (Perkin Elmer), Gene-Amp® buffer (Perkin Elmer) and template.

The radiolabeled PCR products were passed through NucTrap® Probe Purification Columns (Stratagene) and boiled for 5 minutes prior to the addition of approximately $2\times10^6$ CPM to the hybridization mixtures. The blots were incubated overnight at 65° C. and were washed in 1×SSPE, 0.1% SDS at 55° C.–65° C. for approximately 15 minutes. If required, additional washes were performed in 0.1×SSPE, 0.1% SDS.

PCR Primers

The primer sequences for the ~130 bp intron 2 polymorphism were: 5'-AACTCCAGCGACAGAGCTAA-3' (forward) (SEQ ID NO:1), and 5'-TGTATGTACAGAGCCAGTTTCA-3' (reverse) (SEQ ID NO:2). These correspond to bases 5331–5350 and 5458–5437 of GenBank Accession Number L78833 (Smith et al., 1996), respectively. The product was amplified and electrophoresed using standard techniques for genotyping.

Primers which amplified the PCR product across the deletion junction came from sequence contained within probe "C" on the upstream end. Primers on the intron 2 side were placed below an Alu cluster near the distal end of the 7.1 kb EcoRI fragment containing exon 2. The primer sequences for the 1.3 kb external product were: 5'-CCACTGAGGACCTAAAGCATAA-3' (forward) (SEQ ID NO:3), and 5'-GATATTGTAGGGAAAGACTATCAG-3' (reverse) (SEQ ID NO:4). The nested primers used to amplify the 650 bp product were: 5'-GGGATAAGGGAATTAACATTTATGG-3' (forward) (SEQ ID NO:5), and 5'-TTAGCTTTCTTCTGAATGTGAAC-3' (reverse) (SEQ ID NO:6). SEQ ID NO:4 corresponds to bases 10453–10430 of GenBank Accession Number L78833 and SEQ ID NO:6 corresponds to bases 9997–9975 of GenBank Accession Number L78833 (Smith et al., 1996).

PCR reactions were performed with a GeneAmp™ PCR System 9600 thermal cycler (Perkin Elmer), using standard reagents. The external product was amplified for 30 cycles of 94° C. for 15 seconds, 55° C. for 15 seconds, and 72° C. for 1.5 minutes. These reactions were diluted 1:100 and reamplified with nested primers using a similar protocol. To insure that the reactions worked, primers which amplified an ~300 bp product from another locus were included in each mix.

Statistical Analysis

For penetrance estimates, a non-parametric Kaplan-Meier analysis was used to estimate the probability of women developing cancer as a function of age. Unaffected women were classified as censored at their current age or age at death, if deceased.

BIBLIOGRAPHY

American Cancer Society, California (1996). *Cancer Facts and Figures*.
Ariga, T. et al. (1990). *Genomics* 8:607–613.
Boring, C. C. et al. (1994). *CA Cancer J. Clin.* 44:7–26.
Brown, M. A. et al. (1996). *Oncogene* 12:2507–2513.
Cannon-Albright, L. et al. (1994). *Cancer Res.* 54:2378–2385.
Claus, E. B. et al. (1991). *Am. J. Hum. Genet.* 48:232–241.
Easton, D. F. et al. (1993). *Am. J. Hum. Genet.* 52:678–701.
Easton, D. F. et al. (1995). *Am. J. Hum. Genet.* 56:265–271.
Ford, D. et al. (1994). *Lancet* 343:692–695.
Ford, D. et al. (1995). *Am. J. Hum. Genet.* 57:1457–1462.
Gayther, S. A. et al. (1995). *Nature Genet.* 11:428–433.
Hoskins, K. F. et al. (1995). *J. Am. Med. Assoc.* 273:577–585.
Huang, L.-S. et al. (1989). *J. Biol. Chem.* 264:11394–11400.
Kelsey, J. L. (1993). *Epidemiologic Reviews*, Vol. 15.
Malkin, D. et al. (1990). *Science* 250:1233–1238.
Miki, Y. et al. (1994). *Science* 266:66–71.
Narod, S. A. et al. (1995). *Am. J. Hum. Genet.* 56:254–264.
Neote, K. et al. (1990). *J. Clin. Invest.* 86:1524–1531.
Neuhausen, S. L. et al. (1994). *Hum. Mol. Genet.* 3:1919–1926.
Savitsky, K. et al. (1995). *Science* 268:1749–1753.
Schildkraut, J. M. et al. (1988). *Am. J. Hum. Genet.* 45:521–529.
Serova, O. et al. (1996). *Am. J. Hum. Genet.* 58:42–51.
Smith, T. M. et al. (1996). *Genome Res.* 6:1029–1049.
Steichen-Gersdorf, E. et al. (1994). *Am. J. Hum. Genet.* 55:870–875.
Swensen, J. (1996). *BioTechniques* 20:486–491.
Szabo, C. I. and King, M.-C. (1995). *Hum. Mol. Genet.* 4:1811–1817.
Tavtigian, S. V. et al. (1996). *Nature Genetics* 12:333–337.
The Breast Cancer Information Core. http://www.nchgr.nih.gov/Intramural_research/Lab_transfer/Bic/index.html
Wooster, R. et al. (1995). *Nature* 378:789–792.
Xu, C.-F. et al. (1995). *Hum. Mol. Genet.* 4:2259–2264.

What is claimed is:

1. An isolated BRCA1 gene comprising a deletion between two Alu repeat sequences as a result of unequal crossing over between said Alu repeat sequences.

2. The BRCA1 gene of claim 1 wherein one of said Alu repeat sequences occurs within intron 2 of said BRCA1 gene.

3. The BRCA1 gene of claim 1 wherein one of said Alu repeat sequences occurs within a region upstream of exon 1a of the BRCA1 gene.

4. The BRCA1 gene of claim 1 wherein one of said Alu repeat sequences occurs within a region upstream of exon 1a of the BRCA1 gene and wherein a second of said Alu repeat sequences occurs within intron 2 of the BRCA1 gene.

5. A BRCA1 gene which has a deletion comprising exon 1a, exon 1b and exon 2.

* * * * *